(12) United States Patent
Szilák et al.

(10) Patent No.: US 8,647,828 B2
(45) Date of Patent: Feb. 11, 2014

(54) INTRACELLULAR TARGETING OF MOLECULES VIA SYNDECAN-4

(75) Inventors: László Szilák, Szeged (HU); Anikó Keller-Pintér, Csongrád (HU); József Tímár, Budapest (HU); Tamás Letoha, Szeged (HU)

(73) Assignee: Szilak Laboratories Bioinformatics & Molecule-Design Ltd., Szeged (HU)

( * ) Notice: Subject to any disclaimer, the term of this patent is extended or adjusted under 35 U.S.C. 154(b) by 698 days.

(21) Appl. No.: 12/373,557

(22) PCT Filed: Jul. 12, 2007

(86) PCT No.: PCT/IB2007/052787
§ 371 (c)(1),
(2), (4) Date: Mar. 30, 2009

(87) PCT Pub. No.: WO2008/010162
PCT Pub. Date: Jan. 24, 2008

(65) Prior Publication Data
US 2009/0305329 A1 Dec. 10, 2009

(51) Int. Cl.
*G01N 33/567* (2006.01)
(52) U.S. Cl.
USPC .......................................... 435/7.21; 435/7.8
(58) Field of Classification Search
USPC ................................. 435/7.21, 7.8
See application file for complete search history.

(56) References Cited

PUBLICATIONS

Horowitz et al. "Regulation of syndecan-4 phosphorylation in vivo", JBC, 1998, 273(18):10914-10918.*
Horowitz et al. "Phosphatidylinositol-4,5-bisphosphate mediates the interaction of syndecan-4 with protein kinase C", Biochemistry, 1999, 28:15871-15877.*
Koo et al. "Structural basis of syndecan-4 phosphorylation as a molecular switch to regulate signaling", J. Mol. Biol., 2006, 355:651-663. Published online Nov., 2005.*
Oh et al. "Syndecan-4 proteoglycan regulates the distribution and activity of protein kinase C", JBC, 1997, 272(13):8133-8136.*
Tkachenko et al. "Fibroblast growth factor 2 endocytosis in endothelial cells proceed via syndecan-4-dependent activation of Rac1 and a Cdc42-dependent macropinocytic pathway", J of Cell Science, 2004, 117:3189-3199.*
Barth H, Schafer C, Adah MI, Zhang F, Linhardt RJ, Toyoda H, Kinoshita-Toyoda A, Toida T, Van Kuppevelt TH, Depla E, Von Weizsacker F, Blum HE, Baumert TF; Cellular binding of hepatitis C virus envelope glycoprotein E2 requires cell surface heparan sulfate; (2003) J Biol Chem. 278, 41003-12.
Bastiaens PL, Squire A; Fluorescence lifetime imaging microscopy: spatial resolution of biochemical processes in the cell; (1992) Trends Cell Biol. 9:48-52.
Beauvais DM, and Rapraeger AC; Syndecans in tumor cell adhesion and signaling; (2004) Reprod Biol Endocrinol. 2:1-12.
Bernfield M, Kokenyesi R, Kato M, Hinkes MT, Spring J, Gallo RL, Lose EJ; Biology of the syndecans: a family of transmembrane heparan sulfate proteoglycans; (1992) Annu Rev Cell Biol. 8:365-93.
Bobardt Michael D et al.; Syndecan captures, protects, and transmits HIV to T lymphocytes. Immunity Jan 2003, vol. 18, No. 1, Jan. 2003, pp. 27-39.
Carey DJ; Syndecans: multifunctional cell-surface co-receptors; (1997) Biochem J. 327, 1-16.
Choi S, Lee E, Kwon S, Park H, Yi JY, Kim S, Han IO, Yun Y, Oh ES; Transmembrane domain-induced oligomerization is crucial for the functions of syndecan-2 and syndecan-4; (2005) J Biol Chem., 280,42573-9.
Couchman JR, Vogt S, Lim ST, Lim Y, Oh ES, Prestwich GD, Theibert A, Lee W, Woods A; Regulation of inositol phospholipid binding and signaling through syndecan-4; (2002) J Biol Chem. 277, 49296-303.
Horowitz A, and Simons M.; Phosphorylation of the cytoplasmic tail of syndecan-4 regulates activation of protein kinase Calpha; (1998) J Biol Chem. 273(40):25548-51.
HSIA Edward el al.; Nuclear localization of basic fibroblast growth factor is mediated by heparan sulfate proteoglycans through protein kinase C signaling; Journal of Cellular Biochemistry Apr. 15, 2003, vol. 88, No. 6, Apr. 15, 2003, pp. 1214-1225.
Kopatz I, Remy JS, Behr JP; A model for non-viral gene delivery: through syndecan adhesion molecules and powered by actin; (2004) J Gene Med. 6:769-76.
McFall AJ, Rapraeger AC; Identification of an adhesion site within the syndecan-4 extracellular protein domain; (1997) J Biol Chem. 272:12901-4.
OH ES, Woods A, Couchman JR; Multimerization of the cytoplasmic domain of syndecan-4 is required for its ability to activate protein kinase C; (1997) J Biol Chem. 272(18):11805-11.
Park PW, Pier GB, Hinkes MT, Bernfield M; Exploitation of syndecan-1 shedding by Pseudomonas aeruginosa enhances virulence; (2001) Nature. 411, 98-102.
Rue Cary A et al.; Characterization of pseudorabies virus glycoprotein C attachment to heparan sulfate proteoglycans; The Journal of General Virology Feb 2002, vol. 83, No. Pt 2, Feb. 2002, pp. 301-309.
Shafti-Keramat Saeed et al.; Different heparan sulfate proteoglycans serve as cellular receptors for human papillomaviruses; Journal of Virology Dec 2003, vol. 77, No. 24, Dec. 2003, pp. 13125-13135.
Shiau AL, Lin YP, Shieh GS, Su CH, Wu WL, Tsai YS, Cheng CW, Lai MD, Wu CL; Development of a Conditionally Replicating Pseudorabies Virus for HER-2/neu-overexpressing Bladder Cancer Therapy; (2007) Mol Ther. 15:131-8.

(Continued)

*Primary Examiner* — Bin Shen
(74) *Attorney, Agent, or Firm* — Jason D. Voight (57) ABSTRACT

The present invention provides methods for intracellular and/or nuclear targeting of an agent capable of specifically binding to syndecan-4. The present invention further provides methods for the modification of the intracellular and/or nuclear targeting of said agent, as well methods for identifying compounds capable of modifying the syndecan-4 delivery pathway. The present invention further provides experimental kits to perform the methods according to the invention.

11 Claims, 3 Drawing Sheets

(56) References Cited

PUBLICATIONS

Tkachenko E, Lutgens E, Stan RV, Simons M; Fibroblast growth factor 2 endocytosis in endothelial cells proceed via syndecan-4—dependent activation of Rac1 and a Cdc42—dependent macropinocytic pathway; (2004) J Cell Sci. 117 (Pt 15):3189-99.

Tkachenko E, Simons M; Clustering induces redistribution of syndecan-4 core protein into raft membrane domains. J Biol Chem. 277(22):19946-51; Erratum in: J Biol Chem Sep. 20, 2002; 277(38):35778.

Woods A, Couchman JR; Syndecan 4 heparan sulfate proteoglycan is a selectively enriched and widespread focal adhesion component. Mol Biol Cell. Feb. 1994;5(2):183-92.

Woods A and Couchman JR; Syndecans: synergistic activators of cell adhesion; (1998) Trends in Cell Biol. 8, 189-192.

* cited by examiner

SEQUENCE LISTING

```
<160> NUMBER OF SEQ ID NOS: 5

<210> SEQ ID NO 1
<211> LENGTH: 30
<212> TYPE: PRT
<213> ORGANISM: Artificial
<220> FEATURE:
<223> OTHER INFORMATION: from the cytoplasmic domain of syndecan-4
      Ser11 of the sequence equals position Ser179 of the full length
      protein

<400> SEQUENCE: 1

Met Tyr Arg Met Lys Lys Asp Glu Gly Ser Tyr Asp Leu Gly Lys
1               5                   10                  15
```

```
Lys Pro Ile Tyr Lys Lys Ala Pro Thr Asn Glu Phe Tyr Ala
            20                  25                  30

<210> SEQ ID NO 2
<211> LENGTH: 30
<212> TYPE: PRT
<213> ORGANISM: artificial
<220> FEATURE:
<223> OTHER INFORMATION: from the cytoplasmic domain of syndecan-4
      position Ser179 mutated into Glu

<400> SEQUENCE: 2

Met Tyr Arg Met Lys Lys Lys Asp Glu Gly Glu Tyr Asp Leu Gly Lys
1               5                   10                  15

Lys Pro Ile Tyr Lys Lys Ala Pro Thr Asn Glu Phe Tyr Ala
            20                  25                  30

<210> SEQ ID NO 3
<211> LENGTH: 14
<212> TYPE: PRT
<213> ORGANISM: artificial
<220> FEATURE:
<223> OTHER INFORMATION: from the cytoplasmic domain of syndecan-4

<400> SEQUENCE: 3

Met Tyr Arg Met Lys Lys Lys Asp Glu Gly Glu Tyr Asp Leu
1               5                   10

<210> SEQ ID NO 4
<211> LENGTH: 6
<212> TYPE: PRT
<213> ORGANISM: Artificial Sequence
<220> FEATURE:
<223> OTHER INFORMATION: endocytosis signal

<400> SEQUENCE: 4

Lys Arg Lys Arg Lys Arg
1               5

<210> SEQ ID NO 5
<211> LENGTH: 8
<212> TYPE: PRT
<213> ORGANISM: Artificial Sequence
<220> FEATURE:
<223> OTHER INFORMATION: NLS core sequence

<400> SEQUENCE: 5

Arg Met Lys Lys Lys Asp Glu Gly
1               5
```

INTRACELLULAR TARGETING OF MOLECULES VIA SYNDECAN-4

This is the National Stage of International Application PCT/IB2007/052787, filed Jul. 12, 2007.

TECHNICAL FIELD

The present invention provides methods for intracellular and/or nuclear targeting of an agent capable of specifically binding to syndecan-4. The present invention further provides methods for the modification of the intracellular and/or nuclear targeting of said agent, as well methods for identifying compounds capable of modifying the syndecan-4 delivery pathway. The present invention further provides experimental kits to perform the methods according to the invention.

BACKGROUND ART

The four-member family of syndecans belongs to the type I transmembrane proteins that bear heparan sulfate (HS) chains on their extracellular domains (Bernfield et al., 1992). They share similar structure: conserved short, one span transmembrane domain (TM) and the following approximately 30 amino acid length cytoplasmic domain (CD). The N-terminal, divergent extracellular domains (ectodomain) contain three glycosaminoglycan (GAG) attachment sites for heparan sulfate near the N terminus, and may bear chondroitin sulfate at juxtamembrane region (Kokenyesi and Bernfield, 1994). The syndecan-4 ectodomains comprise cell adhesion segments (CBD) mediating cell-cell attachment (McFall and Rapraeger, 1997). Via their heparan sulfate chains the members presented on all adherent cells are capable of binding cell and matrix adhesion molecules, chemokines, growth factors, and extracellular matrix proteins, providing docking surface for microbes, and for viruses (Woods and Couchman, 1998, Beauvais and Rapraeger, 2004, Carey, 1997, Park et al., 2001).

The syndecans are expressed in distinct cell-, tissue-, and developmental stage-specific patterns, thus the syndecan-1, -2, -3 are most abundant in epithelial cells, fibroblasts, and neuronal tissues, respectively, whilst syndecan-4 is expressed ubiquitously, so it is present on virtually all cell types (Bemfield et al., 1992). The syndecans are usually considered as co-receptors, however syndecan-4 had been reported to mediate signals across the membrane via direct activation of protein kinase C alpha (PKCα, Oh et al., 1997). The activation complex of PKCα is regulated by the phosphorylation of Ser179 of syndecan-4 CD (Horowitz and Simons, 1998). When the Ser179 became phosphorylated the syndecan-4-PKCα activation complex fell apart (Couchman et al., 2002).

The syndecan-4 is targeted to lipid rafts, discrete regions of the plasma membrane enriched by cholesterol and sphingolipids. The lipid rafts act as scaffolds for molecules involved in cell adhesion, vesicular trafficking and other signaling cascades. The syndecan-4 is enriched in the focal adhesions and mediates stress-fiber formation, which span the cell and terminate at the focal adhesions anchoring the cell to the extracellular substrata in REF, RPE cell lines (Woods and Couchman, 1994).

The ligand or antibody-mediated clustering leads the redistribution of syndecan-4 to the membrane rafts which later stimulated efficient endocytosis, where the core protein was internalized from the plasma membrane in a lipid raft-dependent, but clathrin-independent manner (Tkachenko et al., 2004). The oligomerization of syndecan-4 molecules assumed the key step towards the downstream signaling (Tkachenko and Simons, 2002, Choi et al., 2005).

The heparan sulfate is supposed as a negatively charged surface to bind and tether big molecules and particles on the cell surface. It was assumed that polycations could penetrate via heparan sulfate (Kopatz et al., 2004). The possible role of heparan sulfates were suggested in binding of viruses and bacteria (Park et al., 2001; Barth et al., 2003), however, there was not suggested any direct mechanism that could support their uptake via any syndecans.

The state of the art presently emphasizes the role of the syndecans as a part of larger membrane protein complexes mostly having extracellularly oriented functions, like in cell adhesion processes, in the mechanism of signal transduction. There is no mention in the art that the members of the syndecan family would be able to specifically carry a ligand into the cytoplasm of the cell or specifically target that ligand into one of the compartment of the cells, although basic fibroblast growth factor (FGF2) could induce the syndecan-4 endocytosis, and the FGF2 internalization was interpreted as a consequence of syndecan-4 endocytosis, and not directly via syndecan-4 (Tkachenko et al., 2004).

However, it was unexpectedly found that syndecan-4, the ubiquitous member of the syndecan family is able to internalize a ligand after specifically binding it via the extracellular domain, and said ligand remains continually attached to the extracellular domain within the cell organelles, and the ligand is being trafficked through the cell compartments along with the syndecan-4. Immunocytochemical staining unraveled that the syndecan-4 complex was present in the early endosomes, in the Golgi apparatus, and it accumulated in the perinuclear region. In addition, it was also found that the syndecan-4 was able to enter the nucleus of the cell, localized mainly with PML bodies and to the nuclear speckles characterized as segments for RNA processing. In addition, it was also found that the nuclear targeting of syndecan-4 delivers the specifically attached ligand into the nucleus of the cell, making possible designing novel targeting systems for agents to be delivered into the nucleus, aiming the RNA processing areas.

DISCLOSURE OF INVENTION

Accordingly, the present invention provides a method for intracellular targeting of an agent capable of specifically binding to syndecan-4, comprising contacting the agent with a cell that comprises syndecan-4 expressed on its cell membrane, and allowing the interaction between said agent and said cell-surface syndecan-4.

In a further embodiment, the present invention relates to a method wherein the agent has been modified to be capable of binding to the extracellular domain of syndecan-4 before allowing said interaction.

In another embodiment, the syndecan-4 expressed on the cell membrane is structurally altered or has an altered expression pattern.

In specific embodiments, the extracellular domain of the altered syndecan-4 is specifically modified to be capable of binding said agent.

In further embodiments the method according of the invention is carried out in vitro.

In further embodiments the method according of the invention is carried out in vivo.

The present invention also relates to a method for intracellular targeting of an agent capable of specifically binding to syndecan-4, wherein said targeting is directed into the nucleus of the cell.

In another embodiment, the method according to the invention comprises a step wherein a nuclear localization signal (NLS) is formed upon cytoplasmic phosphorylation of the cytoplasmic domain of syndecan-4 after said interaction has occurred.

In another embodiment, the method according to the invention comprises phosphorylation at the Ser179 position of the cytoplasmic domain of syndecan-4.

The present invention also relates to a method, wherein said interaction is between one agent and one syndecan-4 molecule.

In a further specific embodiment, the method according to the invention is directed to the intracellular or nuclear transport of a peptide agent.

In another embodiment, the method according to the invention is directed to the intracellular or nuclear transport of a viral agent.

In a specific embodiment, the method according to the invention is directed to the intracellular or nuclear transport of pseudorabies virus (PRV).

In further specific embodiments, the method according to the invention is directed to the intracellular or nuclear transport of a virus used in gene therapy.

In another embodiment, the invention relates to the use of syndecan-4 for facilitating the penetration of a virus into a cell that comprises syndecan-4 expressed on its cell membrane.

The present invention also relates to a method for the modulation of the intracellular targeting of an agent, comprising blocking any of the steps of the syndecan-4 mediated delivery pathway.

In another embodiment, the method according to the invention relates to the modulation of the nuclear targeting of an agent, comprising blocking, inhibiting or inducing any of the steps of the syndecan-4 mediated delivery pathway.

In a further specific embodiment, the method according to the invention comprises the modulation of the formation of an NLS by blocking, inhibiting or inducing the phosphorylation of the cytoplasmic domain of syndecan-4.

In a further specific embodiment, the method according to the invention comprises the modulation of phosphorylation at the Ser179 position of the cytoplasmic domain of syndecan-4.

The present invention also relates to a method for identifying a compound capable of modulating the syndecan-4 mediated intracellular delivery pathway, comprising
  a) contacting an agent known to be specifically targeted into the cell by syndecan-4 with a cell that comprises syndecan-4 expressed on its cell membrane,
  b) allowing the interaction between the agent and the cell-surface syndecan-4,
  c) measuring the intracellular concentration of the agent,
  d) exposing a significantly identical cell to the test compound,
  e) repeating steps a) to c),
  f) identifying the test compound as a specific modulator of the syndecan-4 mediated intracellular delivery pathway if the intracellular concentration of said agent measured in step e) is significantly lower or higher than that measured in step c).

The present invention further relates to a method for identifying a compound capable of modulating the syndecan-4 mediated nuclear delivery pathway, comprising
  a) contacting an agent known to be specifically targeted into the nucleus of a cell by syndecan-4 with a cell that comprises syndecan-4 expressed on its cell membrane,
  b) allowing the interaction between the agent and the cell-surface syndecan-4,
  c) measuring the nuclear concentration of the agent,
  d) exposing a significantly identical cell to the test compound,
  e) repeating steps a) to c),
  f) identifying the test compound as a specific modulator of the syndecan-4 mediated nuclear delivery pathway if the nuclear concentration of said agent measured in step e) is significantly lower or higher than that measured in step c).

In another embodiment, the present invention also relates to a method for identifying a compound capable of modulating the syndecan-4 mediated nuclear delivery pathway, comprising
  a) contacting an agent known to be specifically targeted into the nucleus of a cell by syndecan-4 with a cell that comprises syndecan-4 expressed on its cell membrane,
  b) allowing the interaction between the agent and the cell-surface syndecan-4,
  c) measuring the cytoplasmic phosphorylation of the cytoplasmic domain of syndecan-4 at the Ser179 position,
  d) exposing a significantly identical cell to the test compound,
  e) repeating steps a) to c),
  f) identifying the test compound as a specific modulator of the syndecan-4 mediated nuclear delivery pathway if the phosphorylation of the cytoplasmic domain of syndecan-4 at the Ser179 position is significantly lower or higher than that measured in step c).

In another embodiment, the present invention also relates to an experimental kit for performing the method according to the invention, wherein said kit comprises at least one of the following:
  a cell that comprises syndecan-4 expressed on its cell membrane,
  an agent known to be specifically targeted into the cell by syndecan-4, and
  instructions teaching the method according to the invention.

In a related embodiment, the present invention concerns a method for targeting an agent into the nucleus of a cell, comprising attaching a modified nuclear localization signal (NLS) having any of the sequences of SEQ ID NOs: 2 or 3 to the agent, and introducing the agent-NLS complex or conjugate into said cell.

In another embodiment, the present invention provides a method for altering a transmembrane protein not capable of entering the nucleus so as to be capable of targeting an agent into the nucleus of a cell, comprising introducing the syndecan-4 specific nuclear localization signal (NLS) having any of the sequences of SEQ ID NOs: 1 to 3 into the cytoplasmic domain of said transmembrane protein.

The method according to the present invention comprises the intracellular targeting of an agent capable of specifically binding to syndecan-4, contacting the agent with a cell that comprises syndecan-4 expressed on its cell membrane, and allowing the interaction between the agent and the cell-surface syndecan-4.

The agent capable of specifically binding to syndecan-4 is not limited in any way to any class of biomolecules. Therefore, the agent may be a polypeptide, polysaccharide, nucleic acid or small molecules. If it binds to syndecan-4, it can be targeted into the cell according to the present invention. The ascertain whether any given molecule is able to bind to syndecan-4, the person skilled in the art can perform any appropriate state of the art protocol designed to measure binding between the molecule of the interest and syndecan-4 without undue experimentation. The agent further can be any molecule present in the nature within the living organisms, or it may be an artificial molecule designed to have a specific effect on the organism. In particular, the present invention is especially suitable to facilitate the internalization of different drugs into the cells of interest.

The agent capable of specifically binding to syndecan-4 is not limited in any way to be able to induce the clustering of syndecan-4. According to the state of the art, the clustering of syndecan-4 occurs prior to endocytosis. However, according to the present invention clustering is not prerequisite of the endocytosis, and is not necessary in the case of short oligopeptides, and F(ab) antibody induction.

In the context of the present description, the term polypeptide is intended to mean polypeptides of any length. In particular, basic polypeptides as short as 6 amino acids are able to be internalized by syndecan-4. However, given the presence of the binding between the agent of interest and syndecan-4, proteins as large as full size antibodies (about 200 kDA in molecular weight) may still be internalized according to the method of the present invention. Proteins having modulatory or regulatory effects on metabolism of the cell of interest are especially preferred.

In the context of the present description, nucleic acids can be any type and size poly-nucleotide chains, in particular DNA, RNA, single stranded, double stranded, etc. The agent according to the invention can be especially any type of nucleic acid, which is associated with specific regulatory functions within the cell, or may be antisense or sense sequences designed to modulate the expression of specific genes within the cell of interest. This embodiment of the present invention is especially attractive, because it provides a non-viral cellular delivery method for nucleic acids. It can be foreseen as a major nucleic acid transfection methods for gene therapy, in particular when we consider the fact that the syndecan-4 mediated delivery pathway targets the nucleic acid of interest into the nucleus of the cell when the appropriate signaling conditions are met, as discussed below.

In another preferred case, the agent of the present invention is a drug. After the person skilled in the art established whether the agent of interest is capable of binding to syndecan-4 under any given conditions, the method according to the present invention may by utilized for the delivery of said drug.

Syndecan-4 is expressed ubiquitously, so it is present on virtually all cell types. Therefore, the person skilled in the art usually does not have to perform any extra steps to determine whether the cell of interest expresses syndecan-4 on its surface. However, this measurement may help the person skilled in the art in the optimization of the steps of the method according to the invention, or the determination may show that the level of syndecan-4 on the cell surface is appropriate to the intended targeting protocol. Conversely, where the level of syndecan-4 expressed on the cell surface is too low for the intended application, the person skilled in the art may introduce exogenous syndecan-4 into the cell by using any well-known protocol in the art (this might be useful e.g. in an in vitro drug delivery screening system).

The cell of interest may be present in any type of sample. In particular, the cells may be in a cell or tissue culture, in a biopsy sample, in an intact organ, or may be isolated cells, or the step of contacting the cells and syndecan-4 may be performed in vivo.

It is important to emphasize the fact that the interaction according to the present invention is a specific intermolecular interaction, rather than a non-specific attachment of large molecules/particles to the surface of the cell. In this respect the interaction resembles a ligand-receptor recognition, followed by the ensuing specific steps of events. Therefore, in specific embodiments, the interaction according to the invention between the agent of interest and syndecan-4 may be between one agent and one syndecan-4 molecule. This type of interaction is best exemplified when syndecan-4 is recognized a specific monoclonal antibody, the binding of which is a typical single-molecular attachment, and the bound antibody is internalized by syndecan-4. The unimolecular nature of the interaction does not exclude the possibility of concerted action between the already formed agent-syndecan-4 complexes to carry out the well-known functions of syndecan-4 in the endocytosis processes.

The length of the contacting step may differ in different applications. However, the person skilled in the art will be able to determine the time necessary by using routine optimization without undue experimentation. Typical time to allow the interaction can be as short as a few minutes, or it may be as long as a few hours, preferably between 10 minutes and 3 hours, more preferably between 30 minutes and 2 hours, or about 1 hour.

If necessary, the targeting of the agent can be followed by using state of the art protocols designed for the determination of the amount or presence of the agent in biological samples. In particular, depending of the nature of the agent, immunological methods, nucleic acid hybridization protocols may be used during the internalization process to ascertain the whereabouts of the agent within the cell. This determination may allow the person skilled in the art to further optimize the steps of the method according to the present invention.

In a further embodiment, the method according to the present invention comprises a modified agent, which is modified so as to be capable of binding to the extracellular domain of syndecan-4. In this scenario, the agent in its original form is not capable to bind to syndecan-4, however, by using the information available to the person skilled in the art, the agent of interest is modified to have the binding ability. This modification may involve different alterations, such as but not limited to: covalent cross-linking of a moiety capable to bind syndecan-4 to the agent of interest, non-covalent complex formation between such a moiety and the agent of interest, attachment of anti-syndecan-4 antibody or a fragment thereof to the unmodified agent, etc. One preferred examples of such non-covalent interaction can be the biotin-avidin system. However, releasable attachment may also be envisioned, especially when the active agent is a nucleic acid, and the attachment is performed by using a relatively short complementary nucleic acid that is in turn attached to a moiety capable to bind to syndecan-4.

In any case, the modification should not hinder the ability of the modified agent to bind to syndecan-4 neither the proper functionality of the agent of interest after attaching/complexing with the moiety intended for syndecan-4 binding. The person skilled in the art will be easily able to determine by using protocols generally available whether both said activity of the agent and the syndecan-4 binding capability of any particular conjugate or complex renders said conjugate or complex suitable for the method of the present invention. With standard optimization and directed trial and error experiments the best conjugate or complex can be selected for the agent of interest, and then its intracellular delivery can be accomplished by using the method of the present invention.

In a different embodiment, the syndecan-4 can by modified to be capable of binding the agent of interest, rather than the agent of interest being altered. Preferably, the extracellular domain of the altered syndecan-4 is specifically modified to bind the agent of interest. The modification may target either the protein or the heparin sulfate part of the extracellular domain, and may be based on the information available to the person skilled in the art on the binding properties of said agent. However, standard state of the art procedures will be used for performing said modifications, and testing may be carried out to ensure that said modified syndecan-4 is indeed capable of binding the agent of interest. After creating the specific modifications in syndecan-4, the cells comprising the modified syndecan-4 may be used according to the invention, or the same modification may be introduced into different cells of interest. This way of performing the method of the present invention can be especially suitable for high-throughput screening system.

If specific circumstances require, the two modification approaches may be applied simultaneously to further optimize the efficiency of the internalization protocol according to the present invention.

In addition to, or instead of, having a structurally altered syndecan-4 present on the cell surface, the expression pattern of syndecan-4 may also be altered. The expression of syndecan-4 may be altered by well-known methods available for the person skilled in the art. In particular, expression levels may be altered to increase or decrease the amount of syndecan-4 present on the cell surface, or alternatively, the timing of the expression may by altered, for example by affecting the expression depending on the state of the cell or on the cell cycle. Any method known in the art for said alterations can be preferably incorporated into the protocol according to the invention.

The method according of the invention may be carried out either in vitro or in vivo. In vitro methods can be used for example for the investigation of the syndecan-4 mediated endocytosis pathway or screening the efficacy of drug candidates delivered according to the method of the present invention.

In another preferred embodiment the present method may be used for the delivery of agents to modulate the cell metabolism in vivo. Such targeted therapeutical approaches are widely necessary and fulfils the needs presently sought after in the art. The method according to the invention provides a well-defined, easily adaptable solution for the intracellular delivery of a wide variety of agents e.g. growth factors, heparin binding effectors.

In an especially preferred embodiment, the method according to the invention provides for the intracellular targeting of an agent capable of specifically binding to syndecan-4, wherein said targeting is directed into the nucleus of the cell. As outlined below, and demonstrated in the examples, the syndecan-4 follows a specific path after the internalization, and the agent of interest attached to it is carried along throughout the process. Immunocytochemical staining unraveled that the syndecan-4 complex is present in the early endosomes, in the Golgi apparatus, and is accumulated in the perinuclear region. In addition, it was shown by the present inventors that syndecan-4 is also accumulated in the nucleus of the cell, and localized mainly in the nuclear speckles characterized as segments for RNA processing. As with the previous locales, the agent attached to the syndecan-4 was also carried into the nucleus of the cell, demonstrating the possibility for a nuclear targeting system based on of syndecan-4 to specifically deliver the specifically attached ligand into the nucleus, in particular aiming the RNA processing areas.

Without limiting the invention by theory, it is apparent that the nuclear localization of syndecan-4 and the agent of interest attached thereto is dependent on the phosphorylation of the cytoplasmic domain of syndecan-4, thereby resulting in the formation of a nuclear localization signal (NLS). The present invention provides data that identify this phosphorylation step as necessary to achieve the nuclear targeting. In cultured cells syndecan-4 was able to enter the nucleus only with phosphorylated cytoplasmic domain, without phosphorylation its nuclear presence was not detectable. In a further embodiment, the phosphorylation of the cytoplasmic domain at the Ser179 position is even more preferred.

The present invention also relates to a method for the modulation of the intracellular targeting of an agent by modulating any of the steps of the syndecan-4 mediated delivery pathway. The modulation can be either upregulation or downregulation. The downregulation may be partial or complete, and can be referred to as inhibition or blocking. The modulation can happen at any stage of the delivery pathway, but preferably is accomplished during the extracellular recognition phase. By modulating the specific interaction between the agent of interest and the extracellular domain of syndecan-4, the internalization of said agent can be effectively increased or stimulated, as well as inhibited, or completely blocked.

In particular, this mechanism may play an important role in preventing the endocytosis of viruses and bacteria, for example. An ideal candidate for blocking the extracellular phase of the syndecan-4 delivery pathway can be a specific antibody against the recognition site on the extracellular domain of a specific antibody against the recognition site on the extracellular domain of syndecan-4, which can be tailored according to the specific agent whose delivery is to be blocked. Further candidates may by other agents e.g. small oligopeptides, being capable of covering the recognition site thus blocking the interaction. The selection of the appropriate blocking agent will be done by using well-known screening protocols available in the art for the skilled person.

The person skilled in the art will also readily recognize the importance of the upregulation of the syndecan-4 delivery pathway. This way the uptake of an agent of interest may be facilitated, and the desired targeting thereof may also be increased.

The delivery pathway may be modulated at the time of endocytosis. It is known from the state of the art that the syndecan-4 endocytosis is carried out via small GTP-ases, Arf6 gene, P13 kinase, and other not identified factors. The specific modulation according to the invention of these kinases, enzymes could facilitate, as well as inhibit or stop the mechanism of the endocytosis.

The delivery pathway may also be stimulated or interrupted at any phase of the intracellular stage. The interruption may happen by the disruption of the attachment of the agent to syndecan-4, or especially in the case of nuclear targeting, by preventing the formation of the NLS. This may be done by blocking of the phosphorylation site on the cytoplasmic domain of syndecan-4, or by specifically blocking the activity of the kinases that perform the phosphorylation to for the NLS. Stimulation of the intracellular stage can, for example, be accomplished by the upregulation of the specific intracellular entities participating the regulation of the syndecan-4 delivery pathway The present invention also relates to a method for identifying a compound capable of modulating the syndecan-4 mediated intracellular delivery pathway. The modulation may be either upregulation or downregulation, as discussed above. The identification of such compound can be accomplished by designing an appropriate screening method to follow the syndecan-4-mediated delivery process. The identification protocol may compare the delivery of an agent known to be delivered by syndecan-4 into the cell in the presence and absence of the test compound. The selection criteria for the components of the assay are basically identical to those identified above for the delivery methods according to the inventions. The agent, cells, interaction conditions may be optimized to achieve the best possible internalization efficiency to allow for the optimal identification of potent test compounds.

Test compounds may be selected from different groups of molecules known to act at specific phases of the syndecan-4-mediated delivery pathway. In particular, the screening method may be tailored differently when the test compound, for example an antibody, is suspected to act during the extracellular phase of the delivery process. Conversely, the selection of the components of the screening assay may differ when the test compound is, for example, a known inhibitor or activator of a kinase suspected in participating the intracellular phase of the delivery process, and still other components may be the best suited for candidate compounds for disrupting the endocytic phase of the deliver process.

When the screening assay shows that a compound decrease the rate of the internalization of the standard agent delivered by the syndecan-4-mediated pathway, it can be identified as a specific inhibitor of the pathway, or when the internalization rate is significantly or completely decreased, it can be identified as a blocking agent of the pathway. Conversely, when the screening assay shows that a compound increase the rate of the internalization of the standard agent delivered by the syndecan-4-mediated pathway, it can be identified as a specific inducer or activator of the pathway.

The method according to the present invention can specifically identify a compound capable of modulating the syndecan-4 mediated nuclear delivery pathway. In that case the screening assay will be aimed to detect the nuclear transport of the agent known to be delivered into nucleus of the test cell by the syndecan-4-mediated delivery pathway, and the change in the rate of nuclear transport is measured after addition of the test compound. As above, the test compound will be identified as a specific activator, inhibitor or blocking agent of the syndecan-4 mediated nuclear delivery pathway if the nuclear concentration of the agent is significantly higher or lower, respectively, than that measured in the absence of the test compound.

In another embodiment, the present invention relates to a method for identifying a compound capable of modulating the syndecan-4 mediated nuclear delivery pathway by modulating the cytoplasmic phosphorylation of the cytoplasmic domain of syndecan-4 at the Ser179 position, thereby increasing or decreasing the rate of formation an NLS to direct the transport of the agent into the nucleus of the cell. The components of the assay system again can be optimized to help the detection of specific modulation at the site of the phosphorylation of the cytoplasmic domain of syndecan-4 during the intracellular phase of the deliver process.

In a further embodiment, the present invention relates to a method for targeting an agent into the nucleus of a cell by attaching the syndecan-4 specific nuclear localization signal (NLS) to the agent. The NLS, having the sequence of SEQ ID NO: 1, is responsible for the nuclear targeting of syndecan-4, therefore by attaching it to an agent of interest, the agent will be directed into the nucleus of the cell once it entered the cell. For the attachment of the NLS to the agent, similar considerations may be taken as discussed above for the general modification of the agent to be delivered by the syndecan-4-mediated pathway.

In another embodiment, a modified syndecan-4 specific NLS is attached to the agent.

As it is discussed above, without limiting the invention by theory, the nuclear transport is dependent on the phosphorylation of the cytoplasmic domain of syndecan-4 at the Ser179 position. The present inventors showed that a specific mutation at position 179 is able to form a constitutive NLS without its phosphorylated state. When introducing a Ser179Glu mutation into the corresponding position of SEQ ID NO: 1, the resulting peptide (SEQ ID NO: 2) acts as a nuclear localization signal, and is being directed into the nucleus of the cell. This modified NLS represents an improved, constitutive nuclear delivery pathway that is independent of the formation of the NLS by phosphorylation during the intracellular phase of the delivery process. This embodiment provides added advantages for targeting agents directly into the nucleus of the cells of interest and further enhances the applicability of the present invention. For the attachment of the NLS to the agent, similar considerations may be taken as discussed above for the general modification of the agent to be delivered by the syndecan-4-mediated pathway.

In other preferred embodiments, the NLS sequence can be shortened if the application requires so. As a specific example SEQ ID NO 3_shows one such shortened NLS. The person skilled in the art will be readily able to determine from any shortened sequence based on SEQ ID NO: 1 whether it still is an NLS, or not. It must be noted here that the core sequence of the NLS is apparently present in all syndecans, therefore those can also serve as a source for preparing different localization signals, when their targeting preferences are properly established.

The agent's pathway of entering the cell is not relevant for this embodiment of the present invention. The internalization may happen by any way, which is appropriate for the agent-NLS complex or conjugate. The state of the art describes for example the clathrin- and caveolin-dependent endocytic pathways, which are different from the delivery mechanism according to the present invention. Therefore, these pathways may also be utilized to deliver the agent-NLS conjugate or complex into the cell, and then the NLS directs the nuclear targeting of the complex/conjugate into the nucleus of the cell.

In a further related embodiment, the NLS forming delivery peptide may by modified to contain a different recognition site for different intracellularly expressed kinases. As we discussed above, the formation of NLS makes the nuclear targeting an inducible-type process with the possibility to modulate the efficiency of the nuclear delivery pathway. Accordingly, the introduction of recognition sites of different protein kinases into the nuclear localization signal makes the targeting more widely applicable by allowing the person skilled in the art to use different sequences that are phosphorylated by adequate kinases. As well known for the person skilled in the art, these different kinases may play many different regulatory roles in the cell, and may be expressed during different stages of the cell life or the cell cycle. By incorporating the specific kinase recognition site into the delivery scheme according to the present invention, one will be afforded to choose the optimal time and conditions for the nuclear targeting event, therefore allowing him to apply more intelligently the agent of interest in the nucleus.

In another embodiment, the present invention provides a method for altering a cellular protein not capable of entering the nucleus so as to be capable of targeting an agent into the nucleus of a cell. This is accomplished by introducing the syndecan-4 specific nuclear localization signal (NLS) having the sequence of SEQ ID NO: 1 into said protein to provide more flexibility for the skilled person in the application of the method according to the present invention. Modifying a transmembrane protein having a different recognition capability that syndecan-4, allows the person skilled in the art to utilize that protein for nuclear delivery of its target in case it is otherwise internalized but unable to enter the nucleus not having an appropriate targeting signal on it.

BRIEF DESCRIPTION OF THE DRAWINGS

FIG. 1. Schematic representation of the syndecan-4 mediated delivery pathway. The agent (represented as hexagonal boxes) can attach to the core protein or to the heparan sulfate side chains of syndecan-4 which action is able to trigger the endocytosis of syndecan-4. Syndecan-4, via endosomes and the Golgi apparatus, reaches the perinuclear space, from where it can be oriented into the nucleus with the in situ formed nuclear localization signal (NLS) by phosphorylation of Ser179 (small circles). Syndecan-4 is able to carry and deliver its cargo into the nucleus.

FIG. 2. Syndecan-4 endocytosis was stimulated by FGF2 in HT1080. The time-lapse series of images was acquired at 22° C. The 0 minutes photo was taken without induction (first slab), and the stages of the cells are shown 10, and 60 minutes later after the treatment, respectively.

FIG. 5. Monoclonal anti-GFP serum was applied as endocytosis inducer. Following 60 minutes incubation, the fixed, permeabilized cells were visualized with secondary antiserum against the primary antiserum. Nuclear speckles (strong white formations) were stained sharply in the nucleus.

FIG. 6. The trafficking route of syndecan-4 was detected by organelle specific antibodies. The endocytosed syndecan-4 colocalized with anti-EEAI endosomal marker (A); passed through the trans-Golgi, colocalizing with TGN38 antibody, specific for trans-Golgi (B); and reached the cis-Golgi, appearing together with the cis-Golgi specific GM130 antiserum (C).

The present invention is further illustrated by the experimental examples described below, however, the scope of the invention will by no means be limited to the specific embodiments described in the examples.

EXAMPLE 1

Syndecan-4-GFP Chimeras

Green fluorescent protein (GFP, Clontech; Palo Alto, Calif., USA) labeled fusion proteins were used to follow the process of the endocytosis of syndecan-4 in vivo. GFP was inserted into the syndecan-4 extracellular region in the HuSynd4 pCMV construct, comprising the full, human syndecan-4 cDNA driven by cytomegalovirus (CMV) promoter by using techniques well-known by the person skilled in the art. To avoid possible artifacts, every experiment was repeated with all of the constructs; HuSynd4 pCMV and the GFP chimeras. To reveal the role and the importance of phosphorylation stage of Ser179, mutations were introduced into the cytoplasmic tail region of syndecan-4-GFP chimeras.

The plasmid constructs were introduced in HT1080 fibrosarcoma, MCF7 adenocarcinoma cell lines obtained from ATCC, and maintained according to the ATCC recommendation. The medium, and other cell culture reagents purchased from Cambrex (Santa Rosa, Calif., USA) was complemented with 10% fetal bovine serum (FBS; GIBCO, Bethesda). Confocal microscopy (BioRad-Nikon2000) was used to localise syndecan-4 with its interacting proteins stained by immunocytochemistry, and to follow the coordinated movement of syndecan-4 with time-lapsed techniques by using techniques well-known by the person skilled in the art (Bastiaens and Squire, 1999).

EXAMPLE 2

Internalization of Syndecan-4

Figure 1:
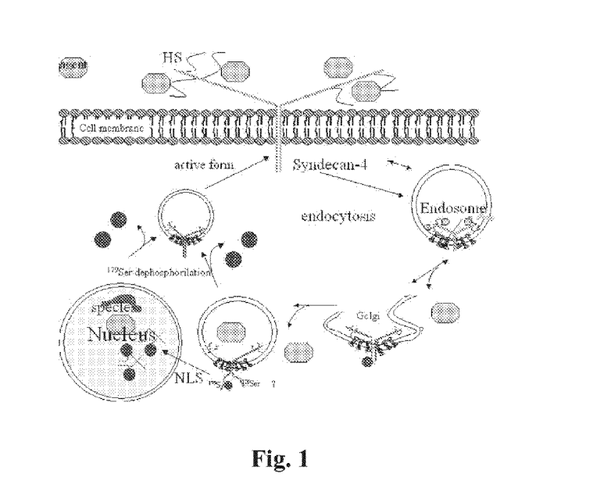
Figure 2:
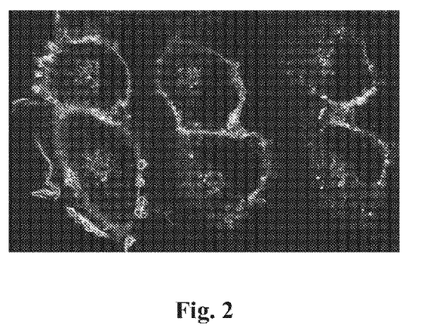
Figure 3:
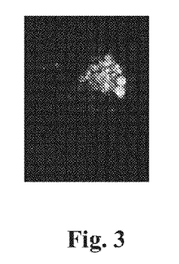
FIG. 3. As a result of the progress of the induced endocytosis, syndecan-4 accumulated in the perinuclear region during 60 minutes incubation.

The endocytosis of syndecan-4 can be triggered in transiently, and stably transfected cells by various treatments, and conditions e.g. addition of basic oligopeptides, FGF2, antibodies and other agents, or serum starvation etc. The trafficking of syndecan-4 and/or with the bound agents was studied by live confocal laser microscopy. Time-lapse series of images were acquired with 1-minute interval for approximately one hour at room temperature (22° C.). The internalization of syndecan-4 was observed immediately after addition of agents into the medium (supplemented 10% FBS). The process of the endocytosis was rather fast, in 15 minutes there was no detectable syndecan-4 in the membrane (FIG. 2). Approximately 30 minutes later the syndecan-4 accumulated in perinuclear compartments, represented as green vesicles. The rate of the process was similar in the cases of different stimulators. By the time the green granules concentrated slowly on one side of the nucleus, asymmetrically, forming several big vesicles within an hour (FIG. 3).

EXAMPLE 3

Specific Internalization of Syndecan-4 Ligands

Figure 4:
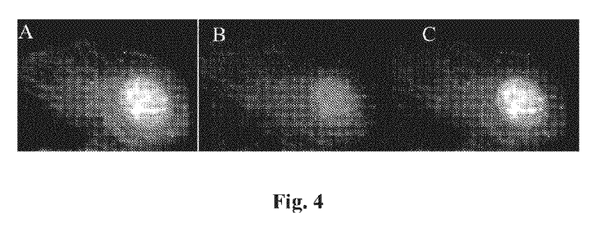
FIG. 4. Colocalization of labeled oligopeptide (A) with syndecan-4 (B) is shown in slab C. The basic oligopeptide could penetrate and travel along with syndecan-4 in the cell, and accumulated in the nucleus (C) in the end. As short as 6 amino acids, KRKRKR (SEQ ID NO: 4) was able to trigger the endocytosis, and penetrate.
Figure 5:
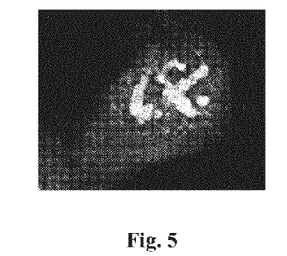

Syndecan-4 is able to carry the agents bound on the cell surface into the cell. Two experiments were carried out. 10 μM of fluorescently (FITC) labeled basic peptides (FIG. 4, sequences in the figure), and antibody against the syndecan-4 ectodomain, or against any epitope inserted into the ectodomain were employed to induce the endocytosis (FIG. 5). The cells were incubated with the basic peptides for an hour, and washed twice with phospho-saline buffer (PBS; Cambrex), fixed in 4% paraformaldehyde. The cells were permeabilized with 0.1% triton X-100 (Sigma, St. Louis, Mo., USA) in PBS, and syndecan-4 was visualized with anti-syndecan-4 ectodomain serum (Zymed, San Francisco, Calif., USA), monitored by immunofluorescent microscopy. In those cases when GFP-syndecan-4 chimera was applied the localization of the chimera molecule was visible without any down stream process. In those cases when antibody induced endocytosis were studied the samples were stained by their fluorescently labeled secondary antibodies. The fluorescently labeled peptides were followed with direct monitoring of the signal. The labeled molecules were detected in distinct compartments of cytoplasm, which indicate that the syndecan-4 was able to internalize and traffic the attached agents, like antibodies, and basic peptides along, holding the specifically bound agents intact throughout the whole process.

EXAMPLE 4

Figure 6:
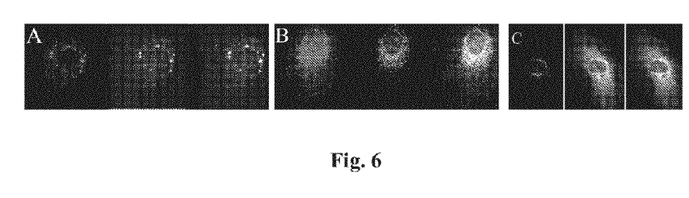

Trafficking of Syndecan-4 from the Cytoplasmic Membrane into Various Cell Compartments The trafficking of syndecan-4 was followed from the plasma membrane to the perinuclear region. To characterize the trafficking route of the internalized syndecan-4, commercially available, specific markers for the different organelles were employed on endocytosis stimulated HT1080, MCF7 lines transfected with different syndecan-4 plasmid constructs. The internalised syndecan-4, and the agents bound to it appeared in the early endosomes co-localizing with early endosomal antigen 1 (EEA 1; ABR, Golden, Colo., USA) (FIG. 6A), then it moved towards the nucleus via the trans-Golgi network (FIG. 6B) and accumulated in the cis-Golgi (FIG. 6C), co-localizing with the TGN38 (BD Biosciences; Palo Alto, Calif., USA, and with the GM 130 (BD Biosci.), which are characterized as trans-, and cis-Golgi resident proteins, respectively. Although most of the syndecan-4 accumulated in the cis-Golgi in the perinuclear region, a well detectable amount of syndecan-4 was found in the nuclei prior to triton-X-100 extraction.

EXAMPLE 5

Delivery of Viral Agents

Pseudorabies virus (PRV), a neurotropic herpes virus has a wide host range of mammals, but it is not pathogenic for humans (Enquist et al., 1998). PRV, therefore, is considered as a potential gene delivery vector (Shiau et al., 2007). In the present experiment, it was studied how the syndecans can intervene in the penetration of PRV. Erythroleukemia K562 cells, characterized as a cell type missing the cell surface heparan sulfate proteoglycan (HSPG), were applied for studying the role of the cell surface HSPG. Among the examined syndecan-1, syndecan-2, syndecan-4, syndecan-4 expression mediated the virus penetration into the cells the most. The expression of the syndecan-2 increased the virus entry 2-fold comparing to the non transfected cells. The expression of syndecan-1 enhanced the virus penetration 3-fold, and the syndecan-4 elevated the number of the infected cells 10-fold. In the case of the of heparan sulfate deficient mutant of syndecan-4, the level of the infection declined to the level of syndecan-2.

The antiserum against the PRV coat protein co-localized with anti-syndecan-4 antiserum, or with the GFP-tagged syndecan-4 on the cell surface and in the cytoplasm proving there is an interaction between the virus coat protein and HSPG syndecan.

EXAMPLE 6

Specific Targeting of Syndecan-4 Ligands into the Nucleus

Figure 7:
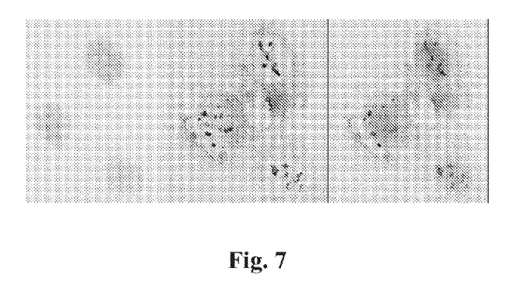
FIG. 7. Syndecan-4 accumulated in some special subnuclear particles called nuclear speckles as a consequence of the endocytosis. The nuclei are dense ovals with pale holes (1st slab), which holes are complemented by the nuclear concentrated syndecan-4 (2nd, 3rd slab). The 1st and 2nd slabs are composited in the 3rd slab.

Smaller amount of syndecan-4 entered the nucleus concentrating in some special nuclear subdomains, like nuclear speckles and PML bodies, where mostly the RNA processing takes place. In certain experiments, approximately up to 10% of the total syndecan-4 was located inside the nucleus. 10 μM of fluorescently (FITC) labeled basic oligopeptides (see FIG. 4 for the sequence) were employed to monitor the nuclear targeting of syndecan-4. The anti-syndecan-4 ectodomain antibody, or the anti-GFP antiserum (Santa Cruz Biotech.; Santa Cruz, Calif., USA) attached to the syndecan-4 ectodomain, or to the GFP-ectodomain fusion protein of syndecan-4-GFP chimera was stained with their fluorophore, secondary antibodies labeling given regions of the nuclei (FIG. 7). FITC labeled basic oligopeptide colocalized with anti-syndecan-4-ectodomain inside the nucleus (FIGS. 4, 5), that is it resided together with the syndecan-4 in the nuclear speckles, the RNA processing region of nuclei (FIG. 7).

EXAMPLE 7

Phosphorylated Ser179CD as Nuclear Targeting Signal

Figure 8:
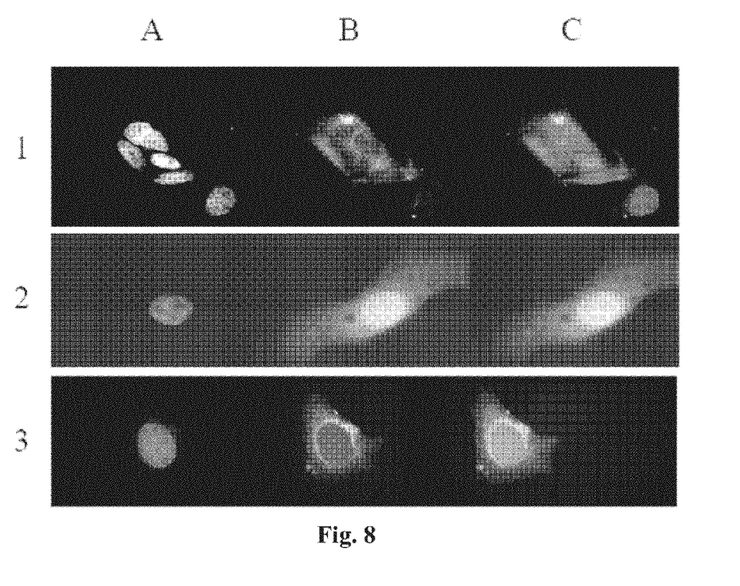
FIG. 8. The Ser179Glu mutated SEQ ID NO: 1 can function as a nuclear localization signal. The sequence of MYRMKKKDEGSYDL (1, SEQ ID NO: 1) was mutated (Ser179Glu (2), and Ser179Ala (3) and fused to GFP reporter. The A panels of the picture show a nuclear staining with Hoechts dye, the B panels show the GFP-chimeras, and in the C panels the channels are united. Most preferably Glu (SEQ ID NO: 3) chimeras were concentrated in the nuclei.

As a consequence of the syndecan-4 endocytosis, the phosphorylation of the syndecan-4 CD occurred. According to the state of the art, the phosphorylation of the CD Ser179 could regulate the syndecan-4-dependent PKC alpha activation. Anti-syndecan-4-phosphorylated-Ser179 (PSer179-CD) antibody (Santa Cruz) showed that the Ser179-phosphorylated syndecan-4 concentrated in the nucleus, characteristically staining the nuclear speckles, and PML bodies (FIG. 7). The unphosphorylated syndecan-4 did not enter the nucleus. The truncated, phosphorylated syndecan-4 CD formed foci in the nuclei, in the same region as the full, showing, that most probably there is a mechanism, which transport the syndecan-4 via the Ser179 phosphorylated CD specifically into given subnuclear particles. Unphosphorylated syndecan-4 was not detectable in the nuclei. It was confirmed by direct cloning of the unphosphorylated CD-GFP chimera (SEQ ID NO: 1), which similarly to the GFP alone, homogenously dispersed in the cells, indicating that the unphosphorylated CD could not serve as nuclear localization signal. However, a GFP-Ser179Glu mutant chimera was a direct reporter into the nucleus, resulting in the nuclear accumulation of the mutated syndecan-4 amino acid sequence (FIG. 8).

EXAMPLE 8

Ser179Glu Mutant as Nuclear Targeting Signal

The phosphorylation of syndecan-4 was mimicked with the change of Ser179 for glutamic acid (E) (SEQ ID NO: 2). A shorter version of the NLS (SEQ ID NO: 3) was also produced. The oligopeptide-GFP reporter fusion proteins were prepared by using standard DNA manipulation procedures. The accumulation of the reporter was detected in the nuclei with both chimeras of SEQ ID NOs: 2 and 3 (FIG. 8).

EXAMPLE 9

Inducible NLS

Any protein characterized as resident in cytoplasm or artificially expressed in a cell can be oriented into the nucleus with the application of either SEQ ID NOs: 2 or 3. However, the phosphorylation of the NLS at the position Ser179 can be achieved by any protein kinase which would capable of phosphorylating said Ser179 position. Therefore, the NLS of the present invention (SEQ ID NO: 1) should be modified to gain a proper kinase site of interest without altering the NLS core sequence (RMKKKDEG (SEQ ID NO: 5)). If the protein kinase is regulatable by any manner is known by a person skilled in the art, the protein can be directed to the nucleus by utilizing different kinase activation pathways. After the creation of this chimera, the protein of interest can be targeted into the nucleus by using any of the above protocols of the examples upon phosphorylation.

EXAMPLE 10

Nuclear Delivery of Agents of Interest

Different agents of interest can be delivered into the cell via syndecan-4 endocytosis. Non-limiting examples of said agents are: nucleic acids, practically DNA cross-linked to any basic protein, that capable of binding to and stimulating the syndecan-4 endocytosis, proteins, oligopeptides, which do not have affinity to syndecan-4, small organic molecules, if linkable to any basic protein, that capable of binding to and stimulating the syndecan-4 endocytosis. The linker peptide may be a basic peptide, preferably lysine (K) and arginine (R) rich peptide, more preferably alternating RK sequences.

The agent of interest (modeled in the present examples by GFP) is conjugated to the exemplary sequence KRKRKR (SEQ ID NO: 4). The resulting molecule is incubated with the targeted cells for an hour, and the protocol is followed as described in Example 3. After detecting the nucleic acid of interest by specific ligands, its localization within the cell and/or nucleus is determined.

REFERENCES

Barth H, Schafer C, Adah M I, Zhang F, Linhardt R J, Toyoda H, Kinoshita-Toyoda A, Toida T, Van Kuppevelt T H, Depla E, Von Weizsacker F, Blum H E, Baumert T F. (2003) Cellular binding of hepatitis C virus envelope glycoprotein E2 requires cell surface heparan sulfate. J Biol Chem. 278, 41003-12.

Bastiaens P I, Squire A. (1992) Fluorescence lifetime imaging microscopy: spatial resolution of biochemical processes in the cell. Trends Cell Biol. 9:48-52.

Beauvais D M, and Rapraeger A C. (2004) Syndecans in tumor cell adhesion and signaling. Reprod Biol Endocrinol. 2:1-12.

Bernfield M, Kokenyesi R, Kato M, Hinkes M T, Spring J, Gallo R L, Lose E J. (1992) Biology of the syndecans: a family of transmembrane heparan sulfate proteoglycans. Annu Rev Cell Biol. 8:365-93.

Carey D J.(1997) Syndecans: multifunctional cell-surface co-receptors. Biochem J. 327, 1-16.

Choi S, Lee E, Kwon S, Park H, Yi J Y, Kim S, Han I O, Yun Y, Oh E S. (2005) Transmembrane domain-induced oligomerization is crucial for the functions of syndecan-2 and syndecan-4. J Biol Chem., 280, 42573-9.

Couchman J R, Vogt S, Lim S T, Lim Y, Oh E S, Prestwich G D, Theibert A, Lee W, Woods A. (2002) Regulation of inositol phospholipid binding and signaling through syndecan-4. J Biol Chem. 277, 49296-303.

Enquist L W, Husak P J, Banfield B W, Smith G A. (1998) Infection and spread of alphaherpesviruses in the nervous system. Adv Virus Res. 51:237-347.

Horowitz A, and Simons M. (1998) Phosphorylation of the cytoplasmic tail of syndecan-4 regulates activation of protein kinase Calpha. J Biol Chem. 273(40):25548-51.

Kopatz I, Remy J S, Behr J P. (2004) A model for non-viral gene delivery: through syndecan adhesion molecules and powered by actin. J Gene Med. 6:769-76.

McFall A J, Rapraeger A C. (1997) Identification of an adhesion site within the syndecan-4 extracellular protein domain. J Biol Chem. 272:12901-4.

Oh E S, Woods A, Couchman J R. (1997) Multimerization of the cytoplasmic domain of syndecan-4 is required for its ability to activate protein kinase C. J Biol Chem. 272(18): 11805-11.

Park P W, Pier G B, Hinkes M T, Bernfield M. (2001) Exploitation of syndecan-1 shedding by Pseudomonas aeruginosa enhances virulence. Nature. 411, 98-102.

Shiau A L, Lin Y P, Shieh G S, Su C H, Wu W L, Tsai Y S, Cheng C W, Lai M D, Wu C L. (2007) Development of a Conditionally Replicating Pseudorabies Virus for HER-2/neu-overexpressing Bladder Cancer Therapy. Mol Ther. 15:131-8.

Tkachenko E, Lutgens E, Stan R V, Simons M. (2004) Fibroblast growth factor 2 endocytosis in endothelial cells proceed via syndecan-4-dependent activation of Rac1 and a Cdc42-dependent macropinocytic pathway. J Cell Sci. 117 (Pt 15):3189-99.

Tkachenko E, Simons M. (2002) Clustering induces redistribution of syndecan-4 core protein into raft membrane domains. J Biol Chem. 277(22):19946-51. Erratum in: J Biol Chem 2002 Sep. 20; 277(38):35778.

Woods A, Couchman J R. (1994) Syndecan 4 heparan sulfate proteoglycan is a selectively enriched and widespread focal adhesion component. Mol Biol Cell. 1994 February; 5(2): 183-92.

Woods A and Couchman J R. (1998) Syndecans: synergistic activators of cell adhesion. Trends in Cell Biol. 8, 189-192.

The invention claimed is:

1. A method for nuclear targeting of an agent capable of specifically binding to syndecan-4, comprising selecting an agent of interest to be targeted into a cell nucleus, contacting said agent with a cell that comprises syndecan-4 expressed on its cell membrane, allowing binding between said agent and the extracellular domain of the syndecan-4 to take place, allowing the internalization of said agent after formation of a complex by the interaction between said agent and said cell-surface syndecan-4, and releasing the agent from the internalized extracellular domain of the syndecan-4 inside the cell membrane, further comprising inducing phosphorylation of the cytoplasmic domain of syndecan-4 resulting in formation of a nuclear localization signal (NLS) on said expressed syndecan-4.

2. The method according to claim 1, wherein the agent has been modified to be capable of binding to the extracellular domain of syndecan-4 before allowing said interaction.

3. The method according to claim 1, wherein the syndecan-4 expressed on said cell membrane is structurally altered or has an altered expression pattern.

4. The method according to claim 3, wherein the extracellular domain of the altered syndecan-4 is specifically modified to be capable of binding said agent.

5. The method according to claim 1, wherein said contacting is carried out in vivo or in vitro and wherein the agent is released in the cell nucleus.

6. The method according to claim 1, wherein said interaction is between one agent and one syndecan-4 molecule.

7. The method according to claim 1, wherein said agent is attached or complexed with a moiety, which moiety binds with the extracellular domain of the syndecan-4 upon allowing said interaction.

8. The method according to claim 1, wherein the NLS is generated or modulated at the Ser179 position of the cytoplasmic domain of syndecan-4.

9. The method of claim 1, further comprising attaching a modified syndecan-4 specific NLS having the sequence of SEQ ID NOs: 2 or 3 to the agent, and introducing the agent-NLS complex or conjugate into said cell.

10. The method of claim 1, further comprising altering a transmembrane protein not capable of entering the nucleus so as to enable it to target an agent into the nucleus of a cell, by introducing the syndecan-4 specific NLS having a sequence selected from the group consisting of SEQ ID NO: 1, SEQ ID NO: 2 and SEQ ID NO: 3 into the cytoplasmic domain of said transmembrane protein.

11. The method of claim 1, further comprising entering of the syndecan-4 from endocytosed vesicles into the cytoplasm of the cell.

\* \* \* \* \*